United States Patent [19]

Sato et al.

[11] Patent Number: 5,785,695
[45] Date of Patent: Jul. 28, 1998

[54] BODY WASTES RECEIVING APPLIANCE

[75] Inventors: Makoto Sato; Kouji Usukura, both of Saitama, Japan

[73] Assignee: Alcare Co., Ltd., Tokyo, Japan

[21] Appl. No.: 745,875

[22] Filed: Nov. 8, 1996

[30] Foreign Application Priority Data

Nov. 10, 1995 [JP] Japan ................. 7-317383

[51] Int. Cl.$^6$ ................. A61F 5/44
[52] U.S. Cl. ................. 604/339; 604/344; 604/338
[58] Field of Search ................. 604/332, 338, 604/339, 342, 344, 345

[56] References Cited

U.S. PATENT DOCUMENTS

| 2,595,934 | 5/1952 | Ginsburg ................. 604/342 |
| 3,089,493 | 5/1963 | Galindo ................. 604/342 |
| 4,816,027 | 3/1989 | Gilchrist et al. ................. 604/339 |
| 4,868,024 | 9/1989 | Cross et al. . |
| 5,009,648 | 4/1991 | Aronoff et al. . |
| 5,209,744 | 5/1993 | Abe et al. ................. 604/332 |
| 5,423,782 | 6/1995 | Wolrich ................. 604/339 |
| 5,591,144 | 1/1997 | Smith et al. ................. 604/332 |

FOREIGN PATENT DOCUMENTS

| 1160550 | 12/1987 | Japan . |
| 244029 | 9/1988 | Japan . |
| 4200470 | 11/1990 | Japan . |
| 6234195 | 12/1991 | Japan . |
| 6304197 | 4/1993 | Japan . |
| 7222768 | 2/1994 | Japan . |
| 2185404 | 7/1987 | United Kingdom ................. 604/332 |

*Primary Examiner*—Robert A. Clarke
*Attorney, Agent, or Firm*—Haverstock, Garrett & Roberts

[57] ABSTRACT

A body wastes receiving appliance constructed in such a manner that the portion which receives body wastes can be easily removed from the appliance and thrown away into a flush toilet or the like, the body wastes receiving appliance including an adhesive plate which has an opening corresponding to a body wastes discharge hole formed in the surface of a human body, a first flange which is fixed the adhesive plate adjacent the non-adhesive side and has an opening corresponding to the opening of the adhesive plate, a second flange which is detachably fitted to the opposite side, with reference to the adhesive plate, of the first flange and has an opening corresponding to the opening of the first flange, an outer pouch which is fixed to the opposite side, with reference to the adhesive plate, of the second flange and has an opening corresponding to the respective openings of the adhesive plate and the first and second flanges, and an inner pouch which is housed inside the outer pouch so as to be separable from the outer pouch and which receives the body wastes discharged through the respective openings of the adhesive plate and the first flange from the body wastes discharge hole, the inner pouch being formed of a water-soluble material.

12 Claims, 6 Drawing Sheets

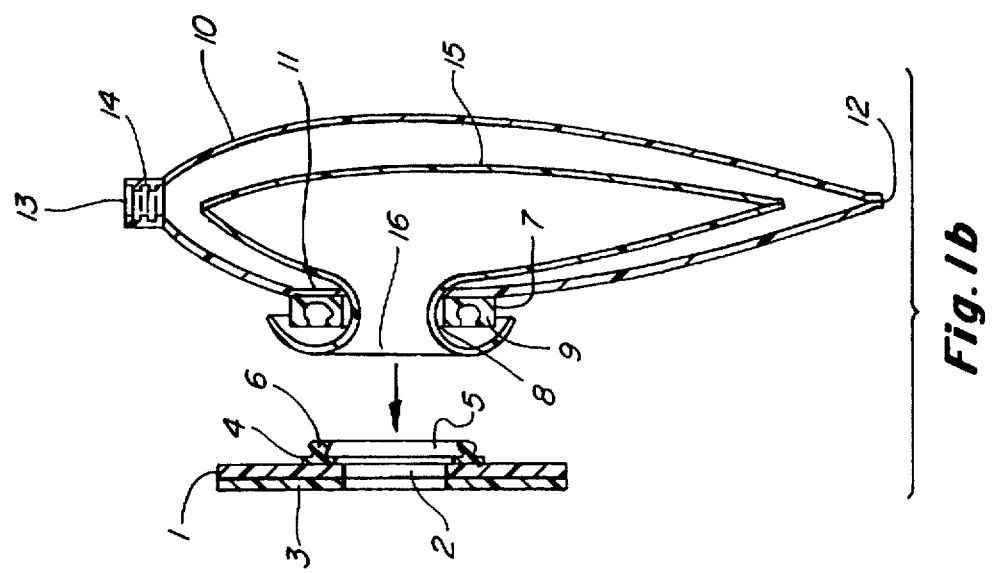
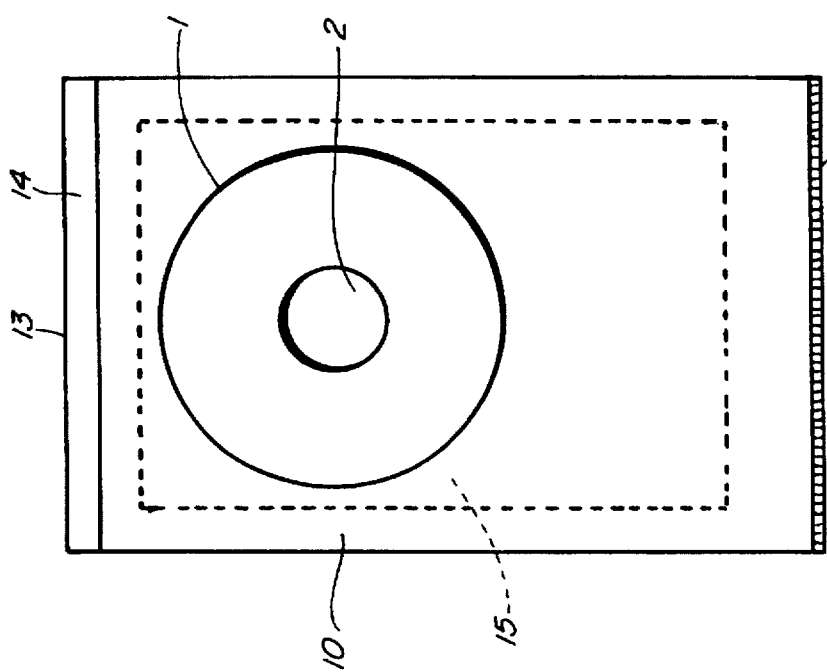
*Fig. 1a*
*Fig. 1b*

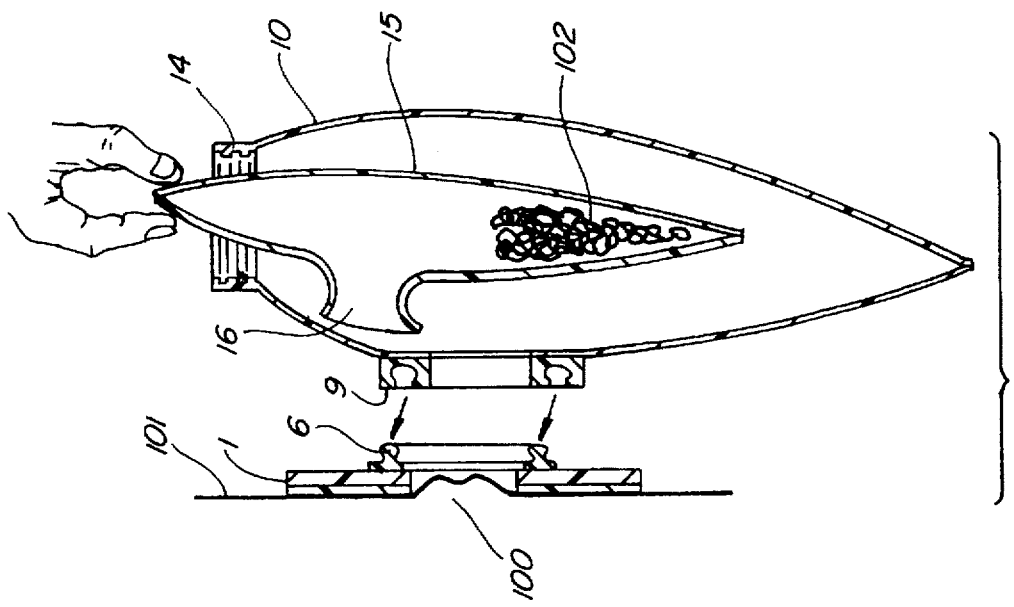
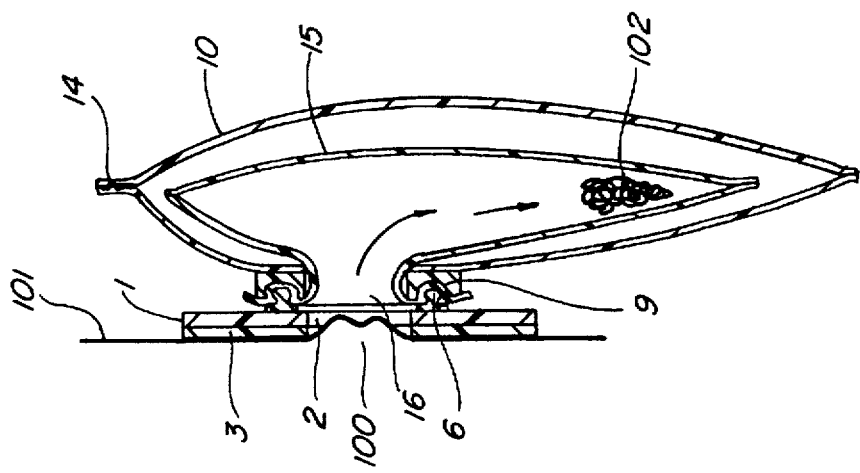

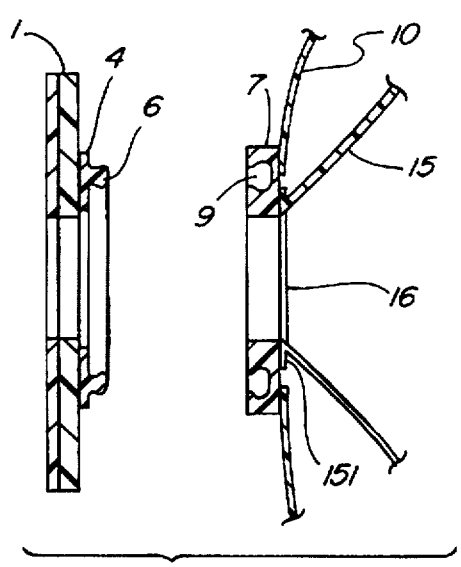
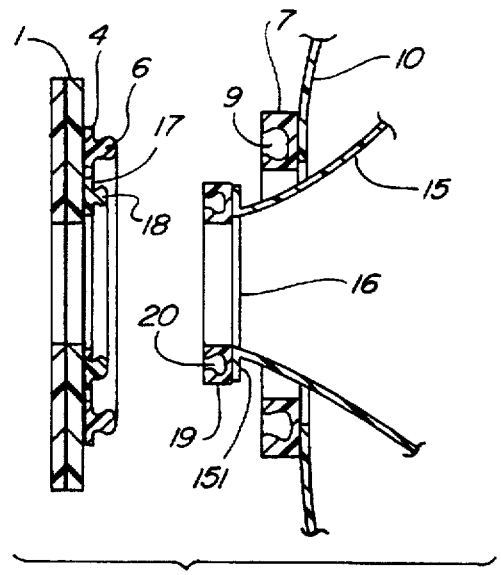
Fig. 4
Fig. 5
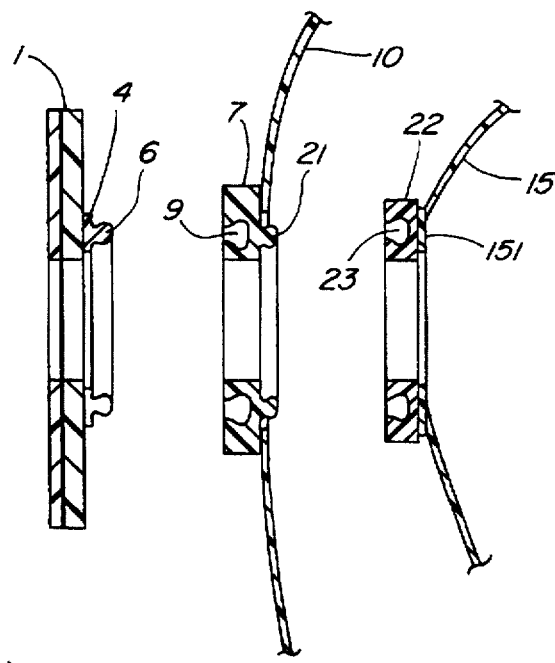
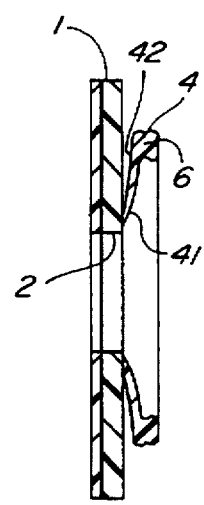
Fig. 6
Fig. 7

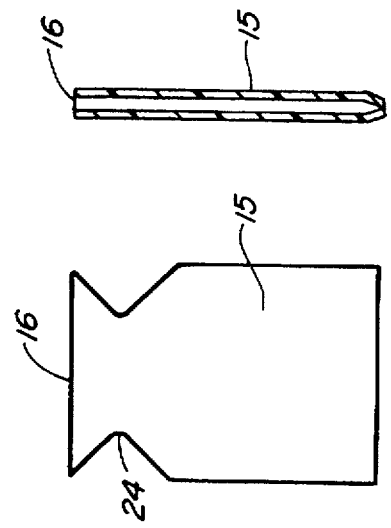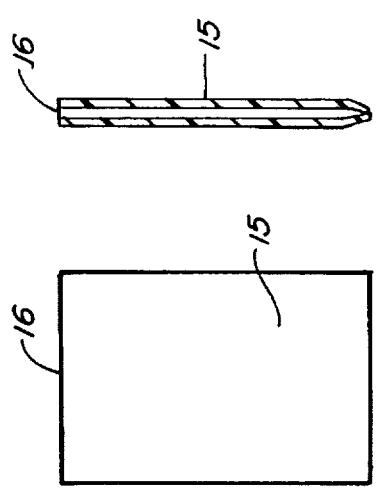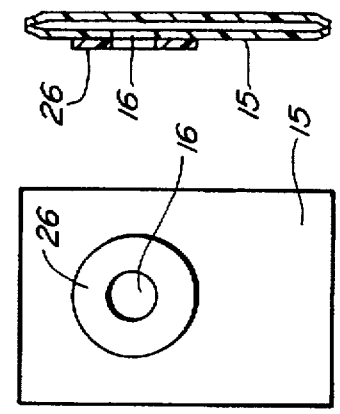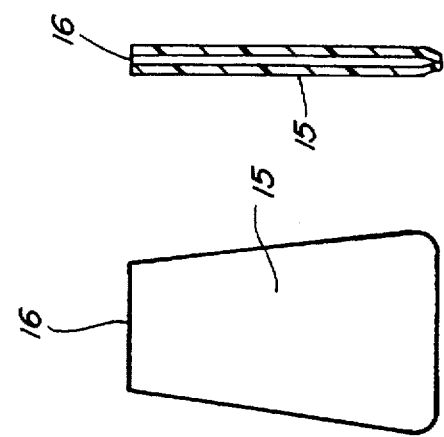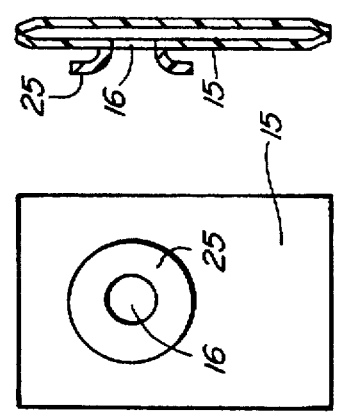

BODY WASTES RECEIVING APPLIANCE

The present invention relates to a human body wastes receiving appliance which is securable around a hole or opening formed through the surface of a human body for receiving and temporarily storing the wastes discharged from the inside of the human body through the hole.

BACKGROUND OF THE INVENTION

Prior Art

A person who has had a surgical operation due to his or her incontinence or inability to control the discharge of feces or urine or a trouble in the digestive organ or urinary organ and, as a result, had a stoma formed on the surface of his or her body in communication with the intestinal tract or ureter, or a person who has had a stoma or fistula formed on the surface his or her body due to a different disease, will typically have a body wastes receiving appliance, which can store the body wastes therein as long as it gives no particular inconvenience to his or her daily life, secured around the wastes discharge opening thus formed on the surface of his or her body in order to dispose of the body wastes such as feces, urine, body fluids, etc. discharged through the opening. Such a body wastes receiving appliance generally comprises an adhesive portion and a wastes receiving portion.

The adhesive portion adheres closely to the surface of a human body around the opening thereon and functions to lead the body wastes to the receiving portion without allowing the leakage thereof and to hold the body wastes receiving portion. In order to enhance the function of the adhesive portion, study and research have been made as to the shape of the adhesive portion and the adhesive material used on the side adhering to the surface of a human body so that the adhesive portion can adhere closely to the peripheral area around the wastes discharge opening in the body surface and cause little skin irritation so that the appliance can be used without fear of leakage or discomfort. As a result, as for the shape of the adhesive portion, there is known at present the technique according to which the part of the adhesive portion corresponding to the peripheral area around the wastes discharge opening of the surface of the human body is made convex or concave in shape so as to adhere closely to the peripheral area around the opening. As for the adhesive material, there have been developed techniques according to which the sweat oozing out from the skin is absorbed to prevent the adhesive force from being weakened, and further, the technique is also known according to which the occurrence of dermatitis due to the skin irritants contained in the body wastes and the breeding of various germs can be prevented.

The body wastes receiving portion is required to have gas barrier properties and flexibility and make no sound and be comfortable to the skin. For instance, as a technical measure for enhancing the gas barrier properties, a single-layer or composite film composed of polyvinylidene chloride, chlorinated polyethylene or the like can be used as the material constituting the pouch in the body wastes receiving portion. Further, in order to provide an enhanced comfortableness to the skin, the pouches can be composed of flexible films, or their surfaces can be embossed, or have a non-woven cloth laid thereon.

There are two known structures for combining the adhesive portion and the body waste receiving portion; one is a one-piece structure, in which both portions are rendered into one integral body, and the other is a two-piece structure in which the two portions are detachably couplable to each other by means of adhesion or fitting. These two structures can be selectively used depending on the intended purpose of use.

As mentioned above, body wastes receiving appliances have so far been improved repeatedly; and thus, almost all of the serious problems in practical use have been solved. However, since the urbanization of life has considerably progressed recently, as a result of which almost all houses are equipped with flush toilets, the body wastes taken out from the appliance can be thrown into a flush toilet but the used wastes receiving portion is not dissolvable in water and therefore should be thrown into the flush toilet; and the wastes receiving portion cannot be disposed of together with general trash, which could lead to a serious social problem on environmental contamination. Thus, the way of disposing of the wastes receiving portion still remains a difficult problem to be solved.

In order to solve this problem, various proposals have been made as to the material for the pouch constituting the wastes receiving portion. In this connection, for instance, the following pouches are known, a pouch formed by coating one surface of a water-soluble film with a hydrophobic material (Japanese Unexamined Utility Model Publication No. (Hei) 2-44029); a pouch formed in such a manner that a hydrophobic coating layer is provided on the inner side of a water-soluble intermediate layer, and a coating layer which is water-resistant but decomposed by alkali is provided on the outer side of the intermediate layer (Japanese Unexamined Patent Publication No. (Sho) 63-63456); a pouch formed by a single or multiple layers composed of a water-soluble oxyalkylene group-containing vinyl alcohol polymer film (Japanese Unexamined Patent Publication No. (Hei) 1-160550); a pouch composed of a biodegradable composite film (Japanese Unexamined Patent Publication No. (Hei) 2-280748); a pouch formed in such a manner that the inner side of a film composed of a water-soluble or water-dispersible polyvinyl alcohol is coated with a water repellent (Japanese Unexamined Patent Publication No. (Hei) 4-200470); a pouch formed in such a manner that the inner side of a film composed of a water-soluble polyvinyl alcohol is coated with a thin layer of polyvinyl alcohol with a low degree of saponification so as to enhance the water permeability of the inner surface (Japanese Unexamined Patent Publication No. (Hei) 6-234195); a pouch formed by providing a protective layer with a weak water insolubility (Japanese Unexamined Patent Publication No. (Hei) 6-304197); and, a pouch formed in such a manner that, on both surfaces of a water-disintegratable absorbing sheet, water-disintegratable sheets are laid (Japanese Unexamined Patent Publication No. (Hei) 7-222768). Most of these pouches are composed mainly of water-soluble films, and the inner sides thereof are provided with protective layers made of water-resistant materials so that the water-soluble films may not be dissolved by the body wastes within a certain specific time, and, with reference to the disposal thereof, the materials of the pouches are required to have very subtle properties in view of the fact that the pouches must be able to be dissolved or disintegrated to such a degree as not to plug up the flush toilet in a short time. Therefore, the control or selection of the material quality of the pouch is difficult. Further during use, the pouches can be broken or rubbed so much as to destroy the protective layers, as a result of which, through the thus damaged portions, the films are dissolved or disintegrated to cause leakage. Thus, these pouches are not popularly used. The types of pouches which are dissolved, when thrown away into flush toilets, with the pH raised pose an environmental problem or the problem of damaging or destroying the flush toilet facilities.

OBJECTS OF THE INVENTION

It is therefore a principal object of the present invention to propose a body wastes receiving appliance constructed in such a manner that, when body wastes are discharged, the portion which directly receives and stores the body wastes can be disposed of easily and cleanly, and can be thrown away is as small in amount as possible and can be dissolved or disintegrated in the water quickly when thrown away into a flush toilet, thus allowing an easy final disposal thereof without causing any trouble to the flush toilet facilities or the water purification facilities, and thus, causing no environmental contamination; and, even if the portion in which the body wastes are be received happens to be broken during use, no injury is inflicted on the wearer and thus the appliance can be used without fear or problems.

SUMMARY OF THE INVENTION

According to the present invention, inside an outer pouch composed of a water-insoluble film, an inner pouch composed of a water-soluble film is disposed so as to be separable therefrom, and body wastes are discharged into only the inner pouch, so that, when body wastes have been discharged, only the inner pouch need be taken out, which is easily done; and if it is directly thrown away into a flush toilet or the like, the inner pouch is quickly dissolved or disintegrated in water, thus causing no environmental pollution at all. Even if the water-soluble film constituting the inner pouch is damaged during use to allow a leakage of the body wastes, they are held in or by the outer pouch, so that the wearer of the appliance does not feel uneasy at all during the wearing thereof, and further, the outer pouch is repeatedly usable and therefore economically advantageous.

According to several preferred embodiments of the invention, the body wastes receiving appliance comprises an adhesive plate having an opening corresponding to a wastes discharge hole or opening formed on the surface of a human body, a first flange fixed to of the adhesive plate adjacent the non-adhesive side thereof and having an opening corresponding to the opening of the adhesive plate, a second flange detachably fixed to the opposite side, with reference to the adhesive plate, of the first flange and having an opening corresponding to the opening of the first flange, an outer pouch mounted at the side, opposite to the adhesive plate, of the second flange and having an opening corresponding to the respective openings of the adhesive plate, the first flange and the second flange, and an inner pouch housed inside of the outer pouch so as to be separable therefrom for receiving the body wastes discharged via the respective openings of the adhesive plate and the first flange from the wastes discharge hole or opening, the outer pouch being formed of a non-water-soluble film, while the inner pouch being formed of a water-soluble film which is dissolved or disintegrated in water, the inner pouch being replaceable.

Further, according to several preferred embodiments of the invention, ring-form fitting portions which are fitted to each other are provided on the side, facing away from the adhesive plate, of the first flange and on the side, closer to the adhesive plate, of the second flange, respectively, so as to be located around the openings of the two flanges, wherein it is desirable for the two flanges to be detachably engaged with each other by fitting. The fitting portions should desirably be constructed in such a manner that one of them is formed as a convex-wise projecting ring, while the other is formed as a ring having the shape of a concave groove matched in shape with the first-mentioned ring, and these fitting portions can be fitted to each other by finger force or manipulation; for which various conventional two-piece type fitting structures can be used. Also, in order to enhance the degree of sealing in the fitting, an O-ring can be incorporated in the fitting portions.

In some of the preferred embodiments, the inner pouch is disposed in such a manner that the peripheral portion around the opening thereof is inserted between the fitting portions of the first flange and the second flange, so that, by fitting the two fitting portions to each other, the inner pouch is coupled to the adhesive plate, whereby the body wastes discharged through the opening of the adhesive plate are received into the inner pouch, and, by replacing the fitting or engagement between both fitting portions, the inner pouch is separated from the adhesive plate and the outer pouch.

Further, in other preferred embodiments the inner pouch has a ring-form water-soluble adhesive member in the peripheral portion around the opening thereof, so that the inner pouch may be detachably mounted or secured to the first flange or to the inner side of the first flange on the surface of the non-adhesive side of the adhesive plate, or to the inner side of the outer pouch at the opposite side, with reference to the adhesive plate, of the second flange.

Besides the first flange and the second flange, a third flange and a fourth flange may be optionally provided, the third flange being disposed inside of the first flange adjacent the non-adhesive side of the adhesive plate and having an opening corresponding to the respective openings of the adhesive plate and the first flange, the fourth flange being formed so as to be detachably fitted to the third flange and having an opening corresponding to the opening of the third flange, wherein, to the opposite side, with reference to the adhesive plate, of the fourth flange, the inner pouch may be attached by adhesion or welding. As the mechanism for engagement and disengagement between the third and fourth flanges, a fitting mechanism similar to the fitting mechanism for the first and second flanges or other suitable fitting structure can be employed.

A further flange can also be optionally provided, which further flange has an opening corresponding to the opening of the second flange and is detachably disposed on the opposite side, with reference to the adhesive plate, of the second flange, in which case the inner pouch may be attached by adhesion or welding to the opposite side, with reference to the adhesive plate, of this flange. As the mechanism for engagement and disengagement between the second flange and the further flange, a suitable fitting mechanism can be employed.

The first flange may be fixed to the non-adhesive side of the adhesive plate by the whole ring-form surface thereof or, alternatively, the first flange may be fixed to the non-adhesive side of the adhesive plate by the ring-form inner peripheral edge portion thereof, with the ring-form outer peripheral edge portion thereof set apart from the non-adhesive side surface of the adhesive plate.

The outer pouch should preferably have, in a portion thereof, a suitable openable/closable mouth through which the inner pouch can be replaced.

The water-insoluble film used for forming the outer pouch should desirably have a high water tightness and excellent gas barrier properties, flexibility and sealing properties. The films used as the pouches of the conventional body wastes receiving appliances can also be used; there can be pointed out single-layer films or composite films made of for instance polyethylene, polyvinylidene chloride, polyvinyl chloride, and chlorinated polyethylene or the materials obtained by blending or copolymerizing vinyl acetate, polyacrylic, acid or the like with the above-mentioned substances. The inner surface of the outer pouch should desirable be embossed or given antistatic treatment in order to prevent the close adhesion thereof to the inner pouch and/or make the inner surface sufficiently slippery.

As the material of the water-soluble film constituting the inner pouch, there are pointed out carboxymethylcellulose, methylcellulose, hydroxypropylmethylcellulose, hydroxyethylcellelose, hydroxypropylcellulose, polyvinyl alcohol, polyvinylpyrolydone, the biodegradable polysaccharide available under the tradename PULLULAN, polyethylene oxide and derivatives or blends of these substances.

As for the material of the water-soluble adhesive member provided in the peripheral portion around the opening of the inner pouch, the above-mentioned water-soluble film or a nonwoven fabric which disintegrates in water can be used as the base, and as the adhesive, for instance, there can be used a composition composed mainly of polyvinyl alcohol, polyvinylmethylether, polyvinylpyrolydone, polyacrylamide or polycarbonic acid and a tackifier blended thereinto.

BRIEF DESCRIPTION OF THE DRAWINGS

FIG. 1a is a front view of one embodiment of a body wastes receiving appliance according to the present invention, including an adhesive plate having a centrally located opening therethrough, a separable outer pouch, and an inner pouch shown in hidden lines contained in the outer pouch;

FIG. 1b is a cross-section view along the longitudinal center line of the appliance of FIG. 1a showing the adhesive plate and outer pouch separated and the placement of the inner pouch in the outer pouch;

FIG. 1c is a longitudinal cross-sectional view of the appliance of FIG. 1a showing the adhesive plate and outer pouch joined together with a portion of the inner pouch secured therebetween and attachment of the adhesive plate to a body surface with the opening of the adhesive plate positioned over a stoma in the body surface and showing body wastes discharged through the stoma collected in the inner pouch;

FIG. 1d is a longitudinal cross-sectional view of the appliance of FIG. 1a showing the outer pouch separated from the adhesive plate and the manual removal of the inner pouch containing body wastes through an opening in the upper end of the outer pouch;

FIG. 4 is a fragmentary cross-sectional view of still another embodiment according to the present invention including an inner pouch provided with a water-soluble, ring-form adhesive member by which the inner pouch is mounted to an inner side of an outer pouch thereof;

FIG. 5 is a fragmentary cross-sectional view of still another embodiment according to the present invention including a further ring-form third flange provided inside a first flange thereof, and a fourth flange securable thereto including a water-soluble, ring-form adhesive member securing the inner pouch thereto;

FIG. 6 is a fragmentary cross-sectional view of another embodiment according to the present invention including a second flange having a convex type ring-form fitting portion adapted for receiving a concave type ring-form fitting portion on the inner pouch thereof;

FIG. 7 is a cross-sectional view of another adhesive plate embodiment according to the present invention including an alternative first flange construction having an outer peripheral portion separated from the adhesive plate;

FIG. 8a is a front view of one embodiment of an inner pouch of the present invention having a rectangular shape;

FIG. 8b is a cross-sectional view of the rectangular shaped inner pouch of FIG. 8a;

FIG. 8c is a front view of an alternative inner pouch construction including a narrowed portion near the opening thereof;

FIG. 8d is a cross-sectional view of the inner pouch of FIG. 8c;

FIG. 8e is a front view of an alternative inner pouch construction having an opening with a flare therearound;

FIG. 8f is a cross-sectional view of the inner pouch of FIG. 8e;

FIG. 8g is a front view of an alternative inner pouch construction including an opening with a water-soluble, ring-form adhesive member therearound;

FIG. 8h is a cross-sectional view of the inner pouch of FIG. 8g;

FIG. 8i shows an alternative inner pouch construction having a shape which gradually narrows towards an opening thereof; and FIG. 8j is a cross-sectional view of the inner pouch of FIG. 8i.

DETAILED DESCRIPTION OF THE PREFERRED EMBODIMENTS

Figure 2B:
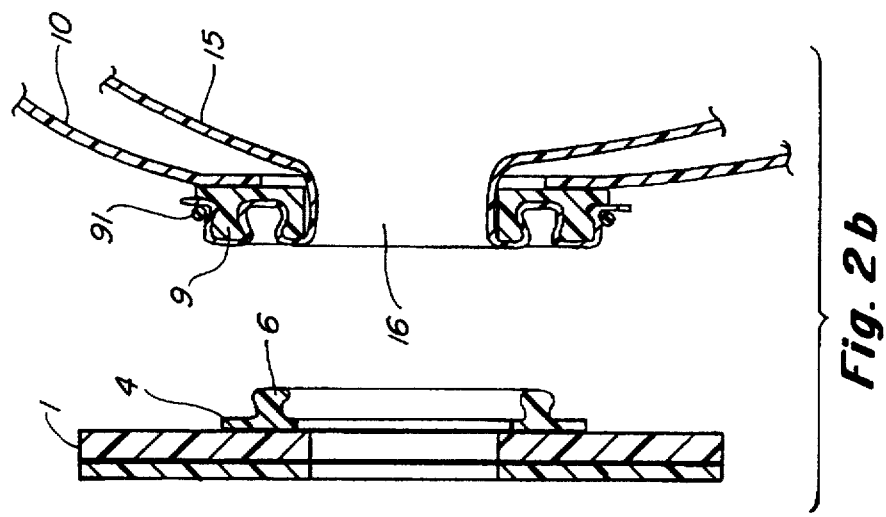
FIG. 2b is a fragmentary cross-sectional view of another body wastes receiving appliance embodiment according to the present invention including a rubber band wound around the fitting portion of the second flange to secure the inner pouch thereof.

Embodiments of the present invention will now be described referring to the drawings by reference numbers wherein like numerals refer to like parts.

FIG. 1a is a front view of an embodiment of the present invention, FIG. 1b is a longitudinal sectional view thereof, and FIG. 1c and FIG. 1d are schematic diagrams illustrating how the embodiment is used. The reference numeral 1 denotes an adhesive plate which is, for instance, round in shape and has an opening 2 in the center thereof. To the adhesive side of the adhesive plate 1, an adhesive layer 3 is provided, while to the surface of the non-adhesive side, i.e. the side opposite to the adhesive side, a ring-form first flange 4 is fixed. First flange 4 has an opening 5 corresponding to the opening 2 of the adhesive plate 1. Along the outer peripheral edge of the first flange 4, a ring-form fitting portion 6 is provided. Numeral 7 denotes a ring-form second flange which is detachably fitted to the first flange 4 and has an opening 8 corresponding to the opening 5 of the first flange 4 and a ring-form fitting portion 9 which has a concave section and can be fitted to the fitting portion 6 of the first flange 4. To the opposite side, with referenced to the fitting portion 9, of the second flange 7, an outer pouch 10 is fixed. The outer pouch 10 is formed of a water-insoluble film and has an opening 11 corresponding to the opening 8 of the second flange 7. A lower end 12 of the outer pouch 10 is sealed, while an upper end 13 thereof has a fastener 14 so as to be opened and closed. In the interior of the outer pouch 10, an inner pouch 15 is inserted. Inner pouch 15 is composed of a water-soluble film which is dissolvable and disintegrates in water. The inner pouch 15 is sealed except for an opening 16. Opening 16 is shaped such that it is once narrowed in its portion adjacent to the opening 11 of the outer pouch 10 and the opening 8 of the second flange 7 so as to be easily drawn out through openings 11 and 8 and then spreads out in the shape of a trumpet horn; and thus, the peripheral portion around the opening 16 of the inner pouch 15 has a significantly wide peripheral area to be pinched between the fitting portion 6 of the first flange 4 and the fitting portion 9 of the second flange 7 when the two fitting portions are fitted together.

Next, the way of using the, body wastes receiving appliance will be described. As shown in FIG. 1c, the appliance is fixed to a body surface 101 by the adhesive layer 3 of the adhesive plate 1 in such a manner that the opening 2 of the adhesive plate 1 faces a body wastes discharge hole or opening such as for instance a stoma 100 formed in the surface of a human body. The fitting portion 9 of the second flange 7 and the fitting portion 6 of the first flange 4 are fitted to each other in such a manner that the tip end portion of the peripheral area around the opening 16 of the inner pouch 15 is disposed so as to cover the fitting portion 6 of the first flange 4 or the fitting portion 9 of the second flange 7, whereby the peripheral portion around the opening 16 of the inner pouch 15 is pinched between the two fitting portions 6 and 9 and thus fixed so as to be liquid tight. As a result, there is formed a path leading from the stoma 100 to the inside of the inner pouch 15 through the opening 2 of the adhesive plate 1, the opening 5 of the first flange 4, and the opening 16 of the inner pouch 15, so that body wastes 102 are sent into the inner pouch 15 as shown by the arrows.

In the case where the inner pouch 15 is to be replaced with a new one after the body wastes are thus received by the inner pouch, the two fitting portions 6 and 9 are disengaged from each other as shown in FIG. 1d, whereby the opening 16 of the inner pouch 15 is disengaged, and thus, by opening the fastener 14 of the outer pouch 10, the inner pouch 15 can be drawn out; and, since the inner pouch 15 is all composed of a water-soluble film, it can be directly thrown away into a flush toilet of the like. Then, a new inner pouch is inserted from the upper end of the outer pouch 10, and the opening portion 16 of the new inner pouch is drawn out through the opening of the second flange 7, and the two flanges 4 and 7 are fitted to each other, whereby the appliance is brought into a usable state again.

Figure 2A:
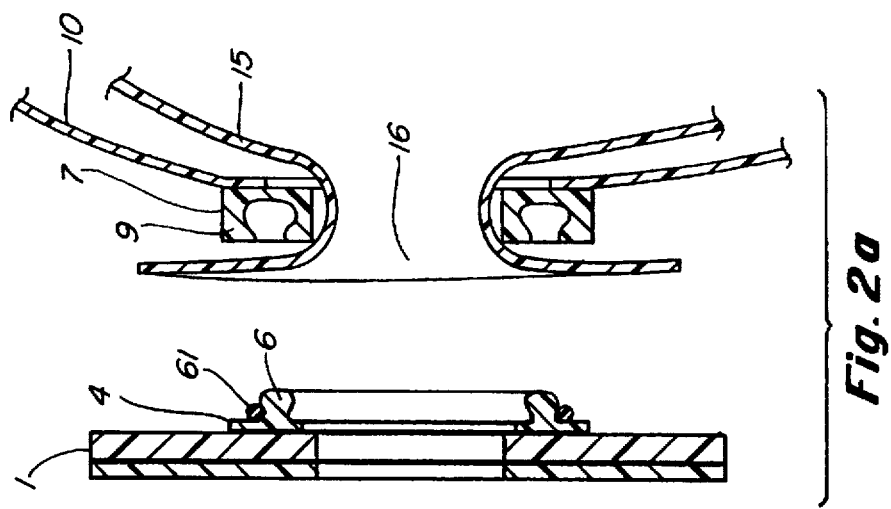
FIG. 2a is a fragmentary cross-sectional view of another body wastes receiving appliance embodiment according to the present invention including an O-ring disposed around the outer periphery of the fitting portion of the first flange thereof.
Figure 2C:
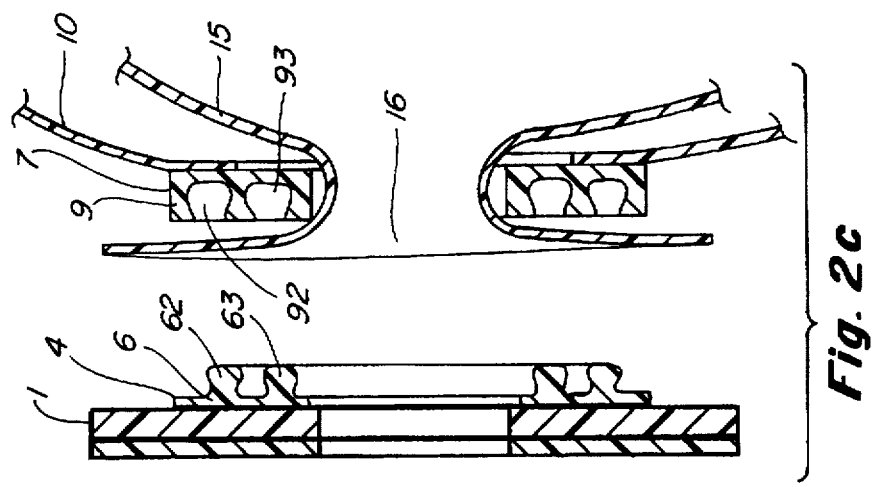
FIG. 2c is a fragmentary cross-sectional view of still another body wastes receiving appliance embodiment according to the present invention including a double-fitting mechanism with two convex type rings on the fitting portion of a first flange thereof and two concave type rings on the fitting portion of a second flange thereof.

As for the structure of the fitting portion 6 of the first flange 4 and the fitting portion 9 Of the second flange 7, there can be used a fitting mechanism similar to the fitting mechanism used in a conventional two-piece type body wastes receiving appliance. FIGS. 2a–2c show several exemplary fitting mechanisms differing from the one shown in FIGS. 1a–d, but portions equivalent to those shown in FIGS. 1a–d are referenced by the same reference numerals. The fitting structure shown in FIG. 2a is constituted in such a manner that an O-ring 61 is additionally disposed around the outer periphery of the fitting portion 6 of the first flange 4, whereby an enhanced sealing function is obtained. The fitting structure shown in FIG. 2b is constituted in such a manner that the peripheral portion around the opening 16 of the inner pouch 15 is put on the fitting portion 9 of the second flange, a rubber band 91 is wound therearound to secure the inner pouch 15, and then the fitting portion 9 is fitted to the fitting portion 6 of the first flange 4; the fitting operation thus being facilitated. The fitting structure shown in FIG. 2c is a double-fitting mechanism constituted in such a manner that the fitting portion 6 of the first flange 4 has two convex type rings 62 and 63, while the fitting portion 9 of the second flange 7 has two concave type rings 92 and 93.

Figure 3:
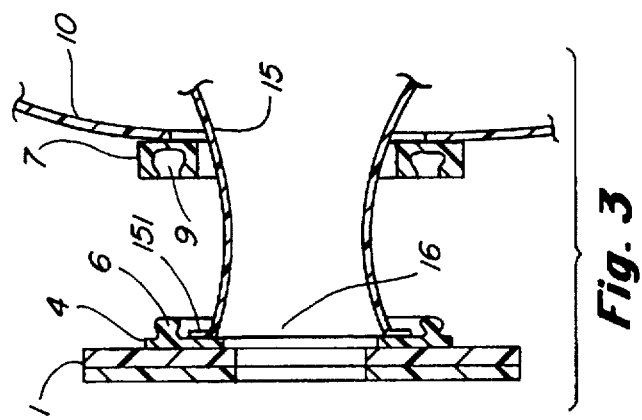
FIG. 3 is a fragmentary cross-sectional view of yet another body wastes receiving appliance embodiment according to the present invention including an inner pouch secured to a fitting portion of a first flange thereof with a water-soluble, ring-form adhesive member.

FIG. 3 is a longitudinal sectional view of a further embodiment, wherein portions corresponding to those shown in FIGS. 1a–d are referenced by the same reference numerals. An inner pouch 15 is provided, in the peripheral area around an opening 16 thereof, with a water-soluble, ring-form adhesive member 151, so that, by means of this adhesive member 151, the inner pouch 15 is mounted or secured to the inner side of the fitting portion 6 at the non-adhesive side of the first flange 4. Since the peripheral portion around the opening 16 of the inner pouch 15 is not inserted between the two fitting portions as in the case of the embodiment shown in FIGS. 1a–d, the inner pouch 15 does not have to have a similar trumpet-shapedly spreading portion or the like. The inner pouch 15 can be torn off from the first flange 4 together with the adhesive member 151 and directly thrown away into a flush toilet or the like. Further, it is alternatively possible to constitute the fitting structure in such a manner that, by means of the adhesive member 151, the inner pouch 15 can be mounted or secured not to the surface of the first flange 4 but directly to the non-adhesive side surface of the adhesive plate.

FIG. 4 is a longitudinal sectional view showing a still further embodiment, wherein, as in the embodiment shown in FIG. 3, an inner pouch 15 is provided with a water-soluble, ring-form adhesive member 151 in the peripheral portion of an opening 16 thereof, but this embodiment differs from the embodiment shown in FIG. 3 in that, in the case of the former, by means of this adhesive member 151, the inner pouch 15 is mounted or secured to the inner side of an outer pouch 10 on the surface, at the opposite side, with reference to the adhesive plate, of not the first flange 4, but the second flange 7. In this embodiment, the inner pouch 15 can be replaced, when it has been used, by a new one in such a manner that the inner pouch 15 is torn off from the second flange 7 together with the adhesive member 151 and the new inner pouch is fixed to the second flange by means of its adhesive member.

FIG. 5 is a longitudinal sectional view of a still further embodiment, wherein portions equivalent to those shown in FIG. 1 are referenced by the same reference numerals. At the non-adhesive side of an adhesive plate 1, a further ring-form third flange 17 is provided inside a first flange 4, and, on the outer peripheral edge thereof, a ring-form fitting portion 18 is formed. An inner pouch 15 is provided with a water-soluble, ring-form adhesive member 151 in the peripheral portion around an opening 16 thereof as in the embodiment shown in FIG. 3, so that, by means of the adhesive member 151, the inner pouch 15 is secured to one side of a fourth flange 19, and, at the other side, that is, the side closer to the adhesive plate, of the fourth flange 19, a ring-form fitting portion 20 corresponding to the fitting portion 18 of the third flange is formed, so that, by fitting the two fitting portions 18 and 20 to each other, the inner pouch 15 is coupled to the adhesive plate 1. The inner pouch 15 may be removed by tearing it off from the fourth flange 19 together with the adhesive member 151 thereof, or the inner pouch may be removed in such a manner that, first, the two fitting portions 18 and 20 are disengaged from each other, and the inner pouch 15 may be drawn out from an outer pouch 10 together with the fourth flange 19, and then the adhesive member 151 is torn off from the fourth flange 19. In the case of the latter method, the new inner pouch can be more easily stuck to the fourth flange 19.

The embodiment shown in FIG. 5 can be modified in such a manner that no adhesive member is provided in the peripheral portion around the opening of the inner pouch, and the inner pouch can be secured to one side of the fourth flange by the use of means such as welding or the like. In this case, the used inner pouch is removed by tearing it off from the fourth flange, but the fourth flange is not re-used; it is thrown away separately from the inner pouch.

FIG. 6 is a longitudinal sectional view of a still further embodiment, wherein portions equivalent to those shown in FIG. 1 are referenced by the same reference numerals. A second flange 7 has a convex type ring-form fitting portion 21 at the side opposite to a fitting portion 9 thereof, that is, the inner side of an outer pouch 10. Numeral 22 denotes a flange for an inner pouch which has, at the side closer to the adhesive plate thereof, a concave type ring-form fitting portion 23 corresponding to the fitting portion 21, and, at the opposite side of the flange 22, there is mounted an inner pouch 15 which has an adhesive member 151 as in the case of the inner pouch shown in FIG. 3. The fitting portions 6 and 9 are fitted to each other, and the fitting portions 21 and 23 are fitted to each other, whereby the inner pouch 15 is coupled to the adhesive plate 1. In this case, the inner pouch 15 may alternatively be fixed to the flange not by means of an adhesive member but by means of welding or the like as described above in connection with the modified embodiment shown in FIG. 5.

In each of the foregoing embodiments and modifications thereof, the first flange is fixed, over the whole surface thereof, to the adhesive plate, but the first flange can be fixed in a state with its outer peripheral portion separated from the adhesive plate. FIG. 7 is a longitudinal sectional view showing an example of such a structure, wherein a first flange 4 is disposed on the non-adhesive side surface of an adhesive plate 1 with an inner ring-form peripheral edge 41 thereof positioned concentrically with an opening 2 of the adhesive plate 1 and fixed to the adhesive plate 1 by welding for instance, in which case the first flange 4 extends outwardly along the non-adhesive side surface of the adhesive plate 1 with an outer peripheral edge 42 of the first flange 4 somewhat separated from the non-adhesive side surface of the adhesive plate 1, and a ring-form fitting portion 6 is provided on the opposite side, with reference to the adhesive plate 1, of the first flange. In the case of this structure, both fitting portions of the first flange and the second flange can be fitted to each other easily by inserting a finger into the space behind the flange 4. This flange structure can be applied not only to the first flange but also to the third flange in one of the foregoing embodiments.

As for the shape of the inner pouch, variously different shapes can be employed. FIGS. 8a-j show front and side views of some embodiments thereof. The inner pouch shown in FIGS. 8a and 8b is of a rectangular shape, which has three sides sealed with an opening 16 in the upper side. The inner pouch shown in FIGS. 8c and 8d has three sides sealed with an opening 16 in the upper side and has a narrowed portion 24 near the opening 16. The inner pouch shown in FIGS. 8e and 8f is constructed in such a manner that, in one surface thereof, an opening 16 is formed with a flare 25 provided therearound, and the four sides are sealed. The inner pouch shown in FIGS. 8g and 8h is constructed in such a manner that, in one surface thereof, an opening 16 is formed with a water-soluble, ring-form adhesive member 26 provided therearound, and the four sides are sealed. The inner pouch shown in FIGS. 8i and 8j is gradually narrowed towards an opening 16 with the remaining three sides sealed. These inner pouches can each be used in any suitable one of the foregoing embodiments.

In the foregoing embodiments, the outer pouches are all of the type which has an opening/closing portion in the upper side thereof, but such opening/closing portion may alternatively be provided in the lower side. Further, as for the way of taking out the inner pouch from the outer pouch for replacement thereof, the way of drawing out the inner pouch from the opening/closing portion of the outer pouch has been described, but the inner pouch can also be drawn out through the opening in the second flange to which the outer pouch is fixed. As for the structure of the fitting portions, the relationship between the convex and concave type ring-form fitting portions in the respective embodiments described above can be reversed.

Thus there has been shown and described several embodiments of body wastes receiving appliances according to the present invention which fulfill all of the objects and advantages sought therefor. It will become apparent to those skilled in the art, however, that many changes, modifications, variations and other uses and applications for the subject body wastes receiving appliances are possible and all such changes, modifications, variations and other uses and applications which do not depart from the spirit and scope of the invention are deemed to be covered by the invention which is limited only by the claims which follow.

What is claimed is:

1. A body wastes receiving appliance comprising:

an adhesive plate having an adhesive side, a non-adhesive side, and an opening therethrough corresponding to a wastes discharge hole or opening formed on the surface of a human body, a first flange secured to the non-adhesive side of said adhesive plate and having an opening corresponding to the opening of said adhesive plate and a ring-form fitting portion, a second flange detachably mounted at the opposite side, with reference to said adhesive plate, of said first flange and having an opening corresponding to the opening of said first flange and a ring-form fitting z portion at the side of the second flange closer to said adhesive plate which is detachably fitted to the fitting portion of said first flange, a third flange secured to the inner side of said first flange at the non-adhesive side of said adhesive plate and having an opening corresponding to the respective openings of said adhesive plate and said first flange, and a ring-form fitting portion, a fourth flange detachable mounted at said third flange and having an opening corresponding to the opening of said third flange and a ring-form fitting portion at the side of the fourth flange closer to said adhesive plate which is detachably fitted to or engaged with the fitting portion of said third flange, an outer pouch secured at the opposite side, with reference to the adhesive plate, of said second flange and having an opening corresponding to the respective openings of said adhesive plate, said first flange, said second flange, said third flange and said fourth flange, and an inner pouch for receiving the body wastes discharged through the respective openings of said adhesive plate, said first flange, said third flange and said fourth flange, said inner pouch being mounted to an opposite side, with reference to the adhesive plate, of said fourth flange and housed inside said outer pouch in such a manner as to be separable therefrom, said outer pouch being formed of a water insoluble film, while said inner pouch being formed of a water-soluble film which is dissolved or disintegrated in water, said inner pouch being replaceable.

2. The body wastes receiving appliance according to claim 1, wherein said inner pouch has a ring-form water-soluble adhesive member in the peripheral portion around the opening thereof, so that, by said adhesive member, said inner pouch is detachably mounted to the opposite side, with reference to the adhesive plate, of said fourth flange.

3. The body wastes receiving appliance according to claim 1, wherein said inner pouch is mounted by welding or heat sealing to the opposite side, with reference to the adhesive plate, of the fourth flange.

4. The body wastes receiving appliance according to claim 1, wherein said first flange is fixed to the non-adhesive side of the adhesive plate over the whole ring-form surface of said first flange.

5. The body wastes receiving appliance according to claim 1, wherein said first flange is fixed to the non-adhesive side surface of said adhesive plate around the ring-form inner peripheral edge of said first flange, while the ring-form outer peripheral edge of said first flange is set apart from the non-adhesive side surface of the adhesive plate.

6. The body wastes receiving appliance according to claim 1, wherein said outer pouch has an openable/closable mouth for replacement of said inner pouch.

7. A body wastes receiving appliance comprising:

an adhesive plate having an adhesive side, an opposite non-adhesive side, and an opening corresponding to a wastes discharge hole or opening formed on the surface of a human body, a first flange secured to the non-adhesive side of said adhesive plate and having an opening corresponding to the opening of said adhesive plate and a ring-form fitting portion, a second flange detachably mounted at the opposite side, with reference to said adhesive plate, of said first flange and having an opening corresponding to the opening of the first flange, a first ring-form fitting portion at the side of the second flange closer to said adhesive plate which is detachably fitted to or engaged with the fitting portion of said first flange and a second ring-form fitting portion at the opposite side, with reference to said adhesive plate, of said second flange, a further flange detachably mounted at the opposite side, with reference to the adhesive plate, of said second flange and having an opening corresponding to the opening of said second flange and a ring-form fitting portion, said ring-form fitting portion of said further flange being fittable to or engageable with said second ring-form fitting portion of said second flange, an outer pouch secured at the opposite side, with reference to said adhesive plate, of said second flange and having an opening corresponding to the respective openings of said adhesive plate, said first flange and said second flange, and an inner pouch for receiving the body wastes discharged through the respective openings of said adhesive plate, said first flange, said second flange and said further flange, said inner pouch being mounted to the opposite side, with reference to the adhesive plate, of said further flange and housed inside said outer pouch in such a manner as to be separable therefrom, said outer pouch being formed of a non-water-soluble film, while said inner pouch being formed of a water-soluble-film which is dissolved in water, said inner pouch being replaceable.

8. The body wastes receiving appliance according to claim 7 wherein said inner pouch has a ring-form water-soluble adhesive member in the peripheral portion around the opening thereof, so that, by said adhesive member, said inner pouch is detachably fixed to the opposite side, with reference to the adhesive plate, of said further flange.

9. The body wastes receiving appliance according to claim 7 wherein said inner pouch has its opening portion mounted by welding or heat sealing to the opposite side, with reference to the adhesive plate, of said further flange.

10. The body wastes receiving appliance according to claim 7 wherein said first flange is fixed to the non-adhesive side of the adhesive plate over the whole ring-form surface of said first flange.

11. The body wastes receiving appliance according to claim 7 wherein said first flange is fixed to the non-adhesive side surface of said adhesive plate at the ring-form inner peripheral edge of said first flange, while the ring-form outer peripheral edge of said first flange is set apart from the non-adhesive side surface of the adhesive plate.

12. The body wastes receiving appliance according to claim 7 wherein said outer pouch has an openable/closable mouth for replacement of said inner pouch.

* * * * *